United States Patent
Whalen et al.

(10) Patent No.: US 7,141,038 B2
(45) Date of Patent: Nov. 28, 2006

(54) ENDOURETHRAL DEVICE AND METHOD

(75) Inventors: Mark J. Whalen, Alexandria, MN (US); Lloyd K. Wihlard, Miltona, MN (US); John M. Reid, Garfield, MN (US)

(73) Assignee: AbbeyMoor Medical, Inc., Prairie, MN (US)

(*) Notice: Subject to any disclaimer, the term of this patent is extended or adjusted under 35 U.S.C. 154(b) by 491 days.

(21) Appl. No.: 10/343,894

(22) PCT Filed: Aug. 7, 2001

(86) PCT No.: PCT/US01/24817

§ 371 (c)(1),
(2), (4) Date: Feb. 4, 2003

(87) PCT Pub. No.: WO02/087412

PCT Pub. Date: Nov. 7, 2002

(65) Prior Publication Data

US 2003/0208183 A1    Nov. 6, 2003

Related U.S. Application Data

(60) Provisional application No. 60/223,345, filed on Aug. 7, 2000.

(51) Int. Cl.
*A61M 29/00* (2006.01)
*A61M 31/00* (2006.01)

(52) U.S. Cl. .................. 604/99.01; 604/101.01; 604/912; 604/919; 604/920; 604/540

(58) Field of Classification Search .......... 604/912, 604/915, 919, 920, 95.03, 96.01, 97.01, 99.01, 604/99.02, 99.03, 99.04, 101.01, 103.01, 604/103.09, 504–544
See application file for complete search history.

(56) References Cited

U.S. PATENT DOCUMENTS

| 2,078,686 | A | 4/1937 | Rowe | 128/255 |
| 2,450,217 | A | 9/1948 | Alcorn | 128/350 |
| 2,687,131 | A | 8/1954 | Raiche | 128/349 |
| 3,136,316 | A | 6/1964 | Beall | 128/350 |
| 3,402,717 | A | * | 9/1968 | Doherty | 128/207.15 |

(Continued)

FOREIGN PATENT DOCUMENTS

WO    WO 00/21462    4/2000

OTHER PUBLICATIONS

WO 02/087412 A3, Nov. 2002, Whalen et al.*

(Continued)

*Primary Examiner*—Tatyana Zalukaeva
*Assistant Examiner*—Michael G. Bogart
(74) *Attorney, Agent, or Firm*—Nawrocki, Rooney & Sivertson, P.A.

(57) ABSTRACT

Several embodiments of an endourethral prosthesis, assembly, and attendant methods are provided for patients presenting with lower urinary tract symptoms (LUTS) or urinary retention. The endourethral prosthesis includes a reversibly expandable element disposed circumferentially about, and longitudinally along a tubular member adapted to receive urine. The tubular member is positionable within a lower urinary tract such that the reversibly expandable element operatively engages a structure of the lower urinary tract so as to prevent migration of the prosthesis so positioned. The reversibly expandable element is in non-reversible fluid communication with the tubular element for selective expansion thereof, the reversibly expandable element is further operatively engagable so as to discharge fluid non-reversibly received from the tubular member exterior to same.

22 Claims, 13 Drawing Sheets

U.S. PATENT DOCUMENTS

| | | | | |
|---|---|---|---|---|
| 3,402,718 A | * | 9/1968 | Doherty | 128/207.15 |
| 3,460,541 A | * | 8/1969 | Doherty | 128/207.15 |
| 3,495,620 A | | 2/1970 | Raimondi et al. | 137/529 |
| 3,630,206 A | | 12/1971 | Gingold | 128/349 |
| 3,642,004 A | | 2/1972 | Osthagen et al. | 128/349 R |
| 3,706,307 A | | 12/1972 | Hasson | 128/2 S |
| 3,726,283 A | * | 4/1973 | Dye et al. | 604/99.03 |
| 3,731,670 A | | 5/1973 | Loe | 128/1 R |
| 3,742,960 A | * | 7/1973 | Dye et al. | 604/99.03 |
| 3,812,841 A | | 5/1974 | Isaacson | 128/1 R |
| 3,908,637 A | | 9/1975 | Doroshow | 128/2 F |
| 4,121,572 A | | 10/1978 | Krzeminski | 128/2 S |
| 4,217,911 A | | 8/1980 | Layton | 128/748 |
| 4,249,536 A | | 2/1981 | Vega | 128/349 B |
| 4,301,811 A | | 11/1981 | Layton | 128/748 |
| 4,407,301 A | | 10/1983 | Streisinger | 128/774 |
| 4,432,757 A | | 2/1984 | Davis, Jr. | 604/99 |
| 4,484,585 A | | 11/1984 | Baier | 128/748 |
| 4,489,732 A | | 12/1984 | Hasson | 128/778 |
| 4,500,313 A | | 2/1985 | Young | 604/280 |
| 4,501,580 A | | 2/1985 | Glassman | 604/43 |
| 4,538,621 A | | 9/1985 | Jarczyn | 128/748 |
| 4,553,533 A | | 11/1985 | Leighton | 128/1 R |
| 4,553,959 A | | 11/1985 | Hickey et al. | 604/96 |
| 4,612,939 A | | 9/1986 | Robertson | 128/774 |
| 4,721,095 A | | 1/1988 | Rey et al. | 128/1 R |
| 4,737,147 A | | 4/1988 | Ferrando et al. | 604/96 |
| 4,781,677 A | | 11/1988 | Wilcox | 604/28 |
| 4,784,647 A | | 11/1988 | Gross | 604/178 |
| 4,792,335 A | | 12/1988 | Goosen et al. | 604/323 |
| 4,865,030 A | | 9/1989 | Polyak | 128/321 |
| 4,865,588 A | | 9/1989 | Flinchbaugh | 604/129 |
| 4,873,990 A | | 10/1989 | Holmes et al. | 128/748 |
| 4,909,785 A | | 3/1990 | Burton et al. | 604/54 |
| 4,932,938 A | | 6/1990 | Goldberg et al. | 604/96 |
| 4,932,958 A | | 6/1990 | Reddy et al. | 606/192 |
| 4,934,999 A | | 6/1990 | Bader | 600/29 |
| 4,946,449 A | | 8/1990 | Davis, Jr. | 604/256 |
| 5,030,199 A | | 7/1991 | Barwick et al. | 600/29 |
| 5,041,092 A | | 8/1991 | Barwick | 604/104 |
| 5,059,169 A | | 10/1991 | Zilber | 604/8 |
| 5,088,980 A | | 2/1992 | Leighton | 600/30 |
| 5,090,424 A | | 2/1992 | Simon et al. | 128/885 |
| 5,100,385 A | * | 3/1992 | Bromander | 604/99.03 |
| 5,112,306 A | | 5/1992 | Burton et al. | 604/101 |
| 5,114,398 A | | 5/1992 | Trick et al. | 600/29 |
| 5,140,999 A | | 8/1992 | Ardito | 128/885 |
| 5,234,409 A | | 8/1993 | Goldberg et al. | 604/96 |
| 5,242,398 A | | 9/1993 | Knoll et al. | 604/101 |
| 5,250,029 A | | 10/1993 | Lin et al. | 604/96 |
| 5,254,089 A | * | 10/1993 | Wang | 604/103.02 |
| 5,271,735 A | | 12/1993 | Greenfeld et al. | 604/266 |
| 5,320,605 A | | 6/1994 | Sahota | 604/101 |
| 5,322,501 A | | 6/1994 | Mahmud-Durrani | 604/8 |
| 5,360,402 A | | 11/1994 | Conway et al. | 604/97 |
| 5,366,506 A | | 11/1994 | Davis | 623/12 |
| 5,380,268 A | | 1/1995 | Wheeler | 600/30 |
| 5,385,563 A | | 1/1995 | Gross | 604/284 |
| 5,403,280 A | | 4/1995 | Wang | 604/96 |
| 5,427,115 A | | 6/1995 | Rowland et al. | 128/756 |
| 5,429,620 A | | 7/1995 | Davis | 604/283 |
| 5,437,604 A | | 8/1995 | Kulisz et al. | 600/30 |
| 5,483,976 A | | 1/1996 | McLaughlin et al. | 128/885 |
| 5,512,032 A | | 4/1996 | Kulisz et al. | 600/29 |
| 5,527,336 A | | 6/1996 | Rosenbluth et al. | 606/192 |
| 5,531,689 A | * | 7/1996 | Burns et al. | 604/99.04 |
| 5,609,583 A | | 3/1997 | Hakki et al. | 604/282 |
| 5,657,764 A | | 8/1997 | Coulter et al. | 128/778 |
| 5,707,357 A | | 1/1998 | Mikhail et al. | 604/96 |
| 5,711,314 A | | 1/1998 | Ardito | 128/885 |
| 5,713,829 A | | 2/1998 | Hakky et al. | 600/29 |
| 5,713,877 A | | 2/1998 | Davis | 604/246 |
| 5,718,686 A | | 2/1998 | Davis | 604/101 |
| 5,724,994 A | | 3/1998 | Simon et al. | 128/885 |
| 5,735,831 A | | 4/1998 | Johnson et al. | 604/280 |
| 5,752,525 A | | 5/1998 | Simon et al. | 128/885 |
| 5,762,599 A | | 6/1998 | Sohn | 600/30 |
| 5,766,209 A | | 6/1998 | Devonec | 604/8 |
| RE35,849 E | | 7/1998 | Soehendra | 604/8 |
| 5,776,081 A | | 7/1998 | Kreder | 600/593 |
| 5,785,641 A | | 7/1998 | Davis | 600/30 |
| 5,813,974 A | | 9/1998 | Guardia | 600/29 |
| 5,864,961 A | | 2/1999 | Vaughan | 33/512 |
| 5,876,417 A | | 3/1999 | Devonec et al. | 606/192 |
| 5,884,629 A | | 3/1999 | O'Brien | 128/885 |
| 5,916,195 A | | 6/1999 | Eshel et al. | 604/96 |
| 5,964,732 A | | 10/1999 | Willard | 604/117 |
| 5,971,967 A | | 10/1999 | Willard | 604/264 |
| 5,976,068 A | | 11/1999 | Hakky et al. | 600/29 |
| 6,004,290 A | | 12/1999 | Davis | 604/96 |
| 6,022,312 A | | 2/2000 | Chaussy et al. | 600/29 |
| 6,033,413 A | | 3/2000 | Mikus et al. | 606/108 |
| 6,056,699 A | | 5/2000 | Sohn et al. | 600/561 |
| 6,083,179 A | | 7/2000 | Oredsson | 600/587 |
| 6,102,848 A | | 8/2000 | Porter | 600/29 |
| 6,105,580 A | | 8/2000 | Von Iderstein et al. | 128/885 |
| 6,132,365 A | | 10/2000 | Sigurdsson | 600/29 |
| 6,167,886 B1 | | 1/2001 | Engel et al. | 128/885 |
| 6,193,646 B1 | | 2/2001 | Kulisz et al. | 600/29 |
| 6,221,060 B1 | | 4/2001 | Willard | 604/264 |
| 6,234,956 B1 | | 5/2001 | He et al. | 600/30 |
| 6,447,462 B1 | | 9/2002 | Wallace et al. | 600/561 |
| 6,494,848 B1 | | 12/2002 | Sommercorn et al. | 600/587 |
| 6,494,879 B1 | | 12/2002 | Lennox et al. | 606/8 |
| 6,527,702 B1 | | 3/2003 | Whalen et al. | 600/30 |
| 6,569,078 B1 | | 5/2003 | Ishikawa et al. | 600/9 |

OTHER PUBLICATIONS

Vicente, J. et al. *Spiral Urethral Prosthesis as an Alternative to Surgery in High Risk Patients with Benign Prostatic Hyperplasia: Prospective Study*. The Journal of Urology. vol. 142. p. 1504. Copyright 1989.

Fabian, K. M. *Der interprostatische "partielle Katheter"*. Urologe. vol. 23, pp. 229-233. 1984.

Fabian, K. M. *Der Intraprostatische "Partielle Katheter"*. Urologe. 1980.

* cited by examiner

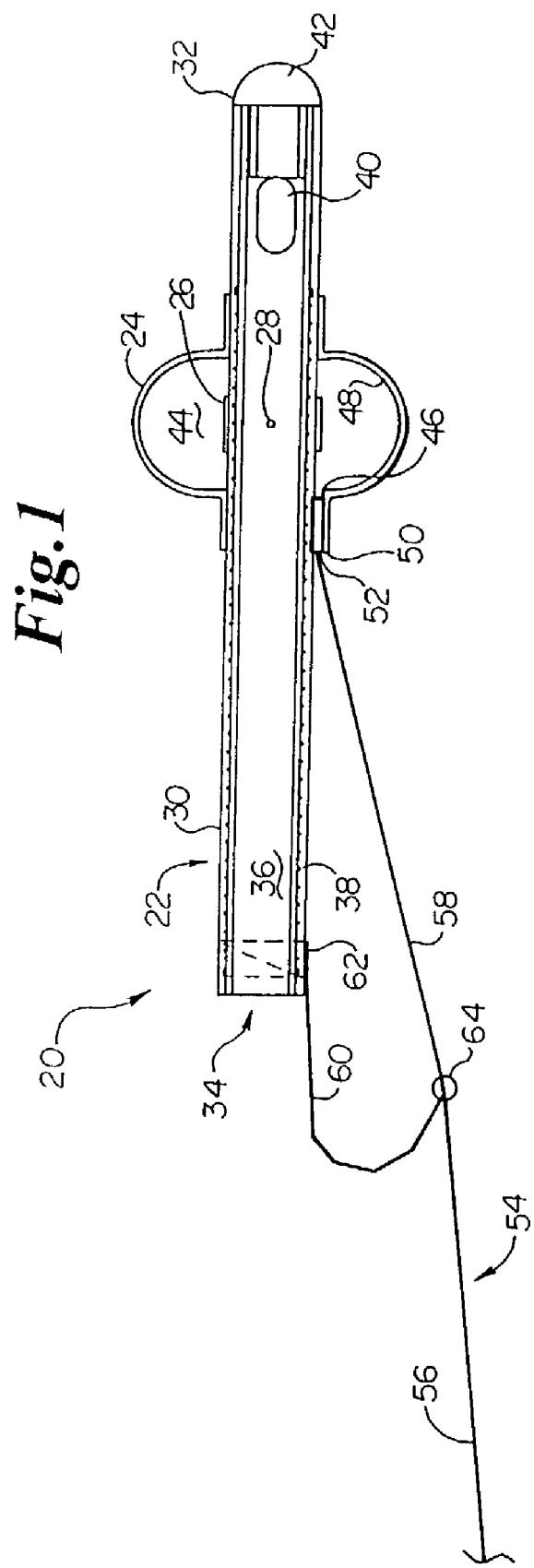

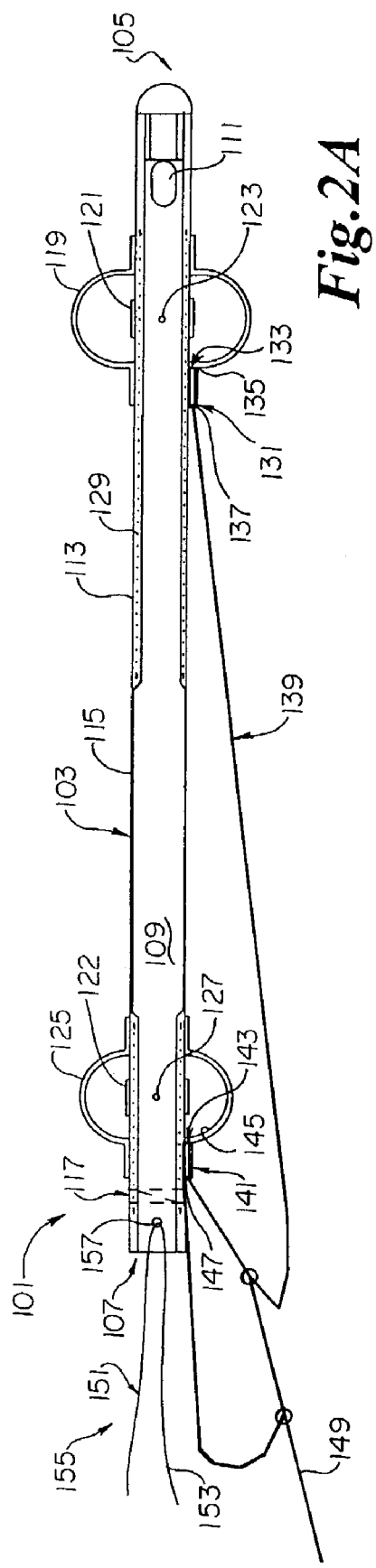

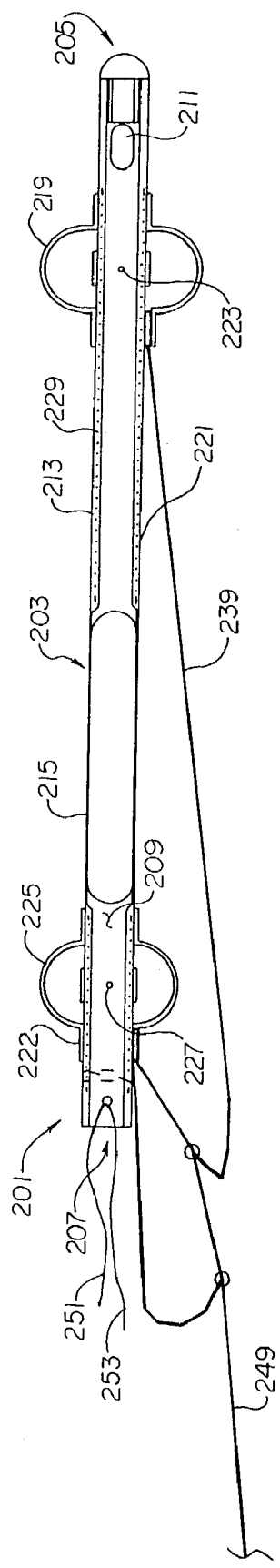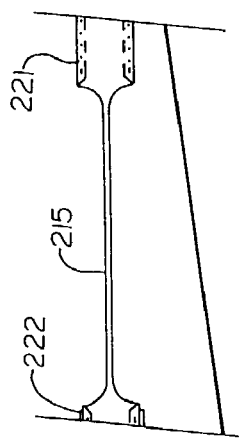

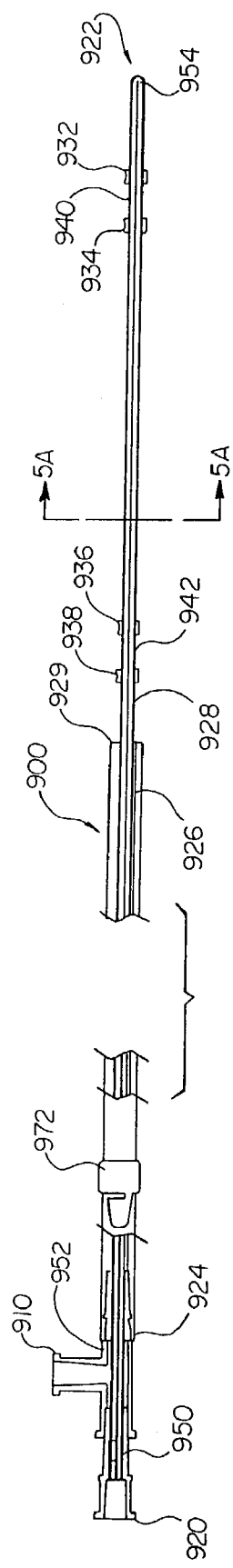
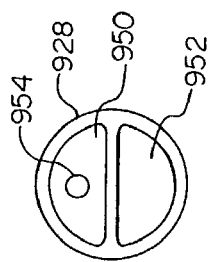

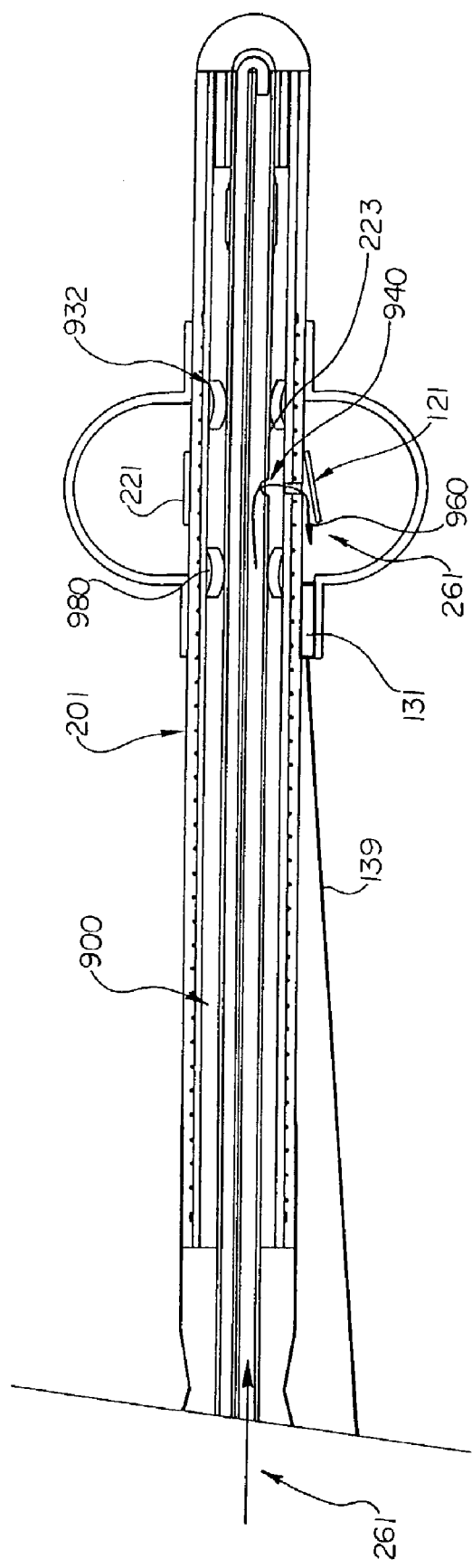

ENDOURETHRAL DEVICE AND METHOD

This is a regular application filed under 35 U.S.C. §111(a) claiming priority under 35 U.S.C. §119(e) (1), of provisional application Ser. No. 60/223,345 having a filing date of Aug. 7, 2000, filed under 35 U.S.C. §111(b).

TECHNICAL FIELD

The present invention generally relates to medical devices, more particularly to endourethral devices, and still more particularly to apparatus, assemblies, and methods for treating urinary retention and or assessing lower urinary tract symptoms.

BACKGROUND OF THE INVENTION

Discharge of bladder contents can be a source of serious and distressing problems for persons whose anatomy is temporarily, or over time, incapable of completely controlling the outflow of urine from the bladder, a clinical condition known as urinary retention. Traditionally, indwelling urethral catheters (i.e., Foley catheters, or the like), in which a free passage is created between the bladder and the outside of the human body in such a way to ensure the permanent flow of urine, have long been used to facilitate bladder drainage in individuals who are unable to initiate or control such drainage due to organic disability, immobility, or other physical impairment, most typically scenarios of acute, rather than chronic, retention. For instance, acute retention is frequently experienced by patients who have recently undergone surgical intervention, either unrelated or related to the urethra. Acute urinary retention is also frequently experienced following radioactive seed implantation within the prostate, cryogenic treatment of the prostate, or minimally invasive procedures performed for the purpose of reducing the volume of the prostate. These include various thermal procedures such as the introduction of microwave energy, heat introduction systems, and chemical injections.

Intraurethral catheters generally permit continuous drainage, or user controlled bladder drainage, with such latter devices typically requiring replacement of, or supplementing the continuous drainage catheter with an incontinence flow control device that enables the user to control bladder discharges through user controlled valves such as those shown, for example, in U.S. Pat. No. 3,812,841 (Isaacson), U.S. Pat. No. 4,909,785 (Burton et al.), U.S. Pat. No. 4,932,938 (Goldberg et al.), U.S. Pat. No. 4,946,449 (Davis, Jr.), and U.S. Pat. No. 5,041,092 (Barwick).

The shortcomings of heretofore known devices have included, but are not limited to, in-situ migration of such devices, a limited indwelling life because of the likely onset of serious urethral infections, and operational complications, most remarkably the cessation of reliable valve functioning, necessitated by the general urinary tract environment (e.g., limited dimensions of the urethra, prolonged device exposure to urine, etc.).

A somewhat related, yet distinct retention solution, in contrast to the traditional indwelling urethral catheter, and those heretofore enumerated urinary flow control devices, has been endourethral stents, or what was initially referred to as the "urological spiral," first developed by Fabian in or about 1978. Generally, the patency of the prostatic urethra is optimally secured by the spiral shape and elastic construction of a coiled, rust-proof, steel urological spiral element. Although chronic infections of the urinary tract and "valve" failure are avoided, since the physiological "valve" function of the man's urethra remains maintained with use of the urological spiral, device migration, deployment difficulties, and debris accumulation and passage, offset any perceived advantages. Later developed prosthetic devices for stenting portions the lower urinary tract integrated inflatable balloons therewith to facilitate placement and positioning of such prosthesis, with heretofore known examples of such devices disclosed in U.S. Pat. No. 5,766,209 (Devonec), U.S. Pat. No. 5,876,417 (Devonec et al.), U.S. Pat. No. 5,916,195 (Eshel et al.), and PCT/US99/23610 (Lennox et al.).

Devonec '209 provide a device having a sphincter responsive sleeve which is sufficiently flexible to conform to the anatomical profile of the urethra and its movements, yet is sufficiently rigid so as to maintain an artificial passage in the urethra. The device is generally supported in the urethra principally by the elastic bearing of the wall of the device segment in radial extension.

Devonec et al. '417 provide a catheter having a indwelling element comprising upper and lower tubular elements, the lower tubular element having an inflatable balloon which circumscribes it. As is readily appreciated with reference to FIGS. 4–9 of Devonec et al. '417, the inflatable balloon functions solely as a positioning device, the indwelling portion being suitably positioned upon abutment of the striated muscular sphincter by the inflated balloon so as to position the deformable portion of the catheter within the sphincter orifice.

Eshel et al. '195 show an internal catheter having proximal and distal tubular members interconnected by a fluid conduit for inflating a balloon attached to the distal tubular member, the device being deliverable using a guiding element which includes a guide balloon for frictionally retaining the device with respect thereto. Once introduced into the urethra, the device balloon is positioned to be within the urinary bladder, and inflated so as to temporarily anchor the catheter at a required position such that a segment of said tubular member is located at the prostatic urethra. The positioning of one of the tubular members at one side of the sphincter, and the other tubular member at the other side of the sphincter, is alleged to effectively anchor the catheter in place, such that after extraction of the guide element, the device balloon is deflated (i.e., the distal device balloon is used as a locating mechanism, rather than a anchoring mechanism).

Lennox et al. '23610 likewise make use of an inflatable balloon for inserting a prosthesis into the urethra of a patient. More particularly, in the deployment methodology, the prosthesis, the pusher, the inflation cannula, and the balloon are inserted into a urethra of the patient. The prosthesis is pushed by the pusher along with the inflation cannula until a drainage hole of a first tubular element is positioned within the bladder. Thereafter, the balloon is inflated via the inflation cannula, the prosthesis thereafter being withdrawn until resistance is felt. This resistance indicates that the balloon is contacting the opening of the bladder just above the prostate. After appropriate positioning, the deployment apparatus including the balloon may be retracted in furtherance of removal.

Due to a general lack of reliable device performance (e.g., continued device migration, increasing device and deployment complexity, generally cumbersome overall device structure, etc.), heretofore known stenting devices served a single purpose, namely as a retention solution, and did so with a variety of shortcomings. With no reliable, straight forward differential diagnosis options being generally accepted and practiced, males presenting with non-retention symptoms have had no diagnostic options short of invasive irreversible medical procedures (e.g., surgery, thermal treatment, etc.).

Presently, millions of men in the United States alone exhibit some form of lower urinary tract symptoms (LUTS), with bladder outlet obstructions (BOOs), being a major subgroup of LUTS. BOOs are primarily caused by the enlargement of the prostrate gland (e.g., benign prostate hyperplasia (BHP)) which results in radial compression of the urethra surrounded thereby (i.e., the prostatic urethra), thus obstructing (i.e., constricting) urine flow, resulting in incomplete emptying of the bladder (i.e., there being what is clinically referred to as a "post void residual" (PVR) remaining in the bladder). Heretofore, such symptoms would be treated by using surgical procedures such as trans urethral resection of the prostate (TURP), or non-surgical procedures such as thermal treatment of the prostate.

As alluded to herein above, three inter-dependent, easily-measured parameters may be ascertained and assessed in furtherance of increased understanding of the patient's urodynamic status, namely, PVR, volumetric flow (i.e., discharge rate) of urine from the bladder, and voiding pattern(s) readily established via maintenance of avoiding diary (i.e., evaluation of about one week's worth of voiding specifics).

The first parameter, PVR, is determined using ultrasound imaging of the bladder, with a retained urine volume calculated and recorded post void. Although there exist a variety of clinical data on the matter, it is generally believed that a PVR value of about <100 cc is considered a "successful" void, with a PVR value in excess of about 300 cc being cause for serious concern, or at least cause for further inquiry into the subject's void patterns, etc. For example, a subject with an "abnormal" PVR (i.e., symptomatic PVR) will often need to urinate more frequently, and-is likely to experience physical discomfort, such as frequent urges to urinate, as well as physical exhaustion due to sleep deprivation (i.e., nocturia). Symptomatic PVR is typically associated with either hyperplasia (i.e., thickening) of the prostatic gland, or a bladder that is not functioning properly due to decompensation of the muscular function. It is this diagnostic differentiation that has heretofore been unrealized in a simple, straight forward and reliable manner.

The second parameter, urine discharge rate during emptying of the bladder, is a strong indicator of the function of the bladder when obstruction via the prostate is not present. Typical urine discharge rates for "healthy" males is in excess of about 12 cc/s, with a diminished discharge flow rate of about <5 cc/s generally believed to be indicia of BOO.

Due to the fact that BOO patients are only a subgroup of patients with LUTS, proper treatment of the specific problem requires complete knowledge of the urodynamic status of the patient in order determine whether the patient's symptoms are caused by BOO, or from bladder deficiencies (e.g., bladder decompensation), or sphincter dysnergia. While comprehensive knowledge of the bladder-urethra interaction during urination may be obtained using complex urodynamic procedures, and urethra pressure profiling, most urologists are currently reluctant to perform such procedures prior to invasive, or minimally invasive, procedures directed to debulking the prostatic urethra.

Thus there remains a need, in addition to traditional therapeutic application of an improved endourethral device for subjects in retention, for improved diagnostic confidence for LUTS patients, more particularly, a differential diagnostic that is low risk, reliable, and least cost. Accordingly, it is desirable to provide additional, improved device and procedural options for the care and diagnosis of patients who present to the urologist with LUTS, or patients who experience acute retention or chronic retention.

SUMMARY OF INVENTION

The subject invention, whether it be the apparatus, the assembly, or the methodology, provides additional treatment options for patients exhibiting LUTS and or urinary retention. Additionally, the subject invention provides for the easy acquisition of reliable diagnostic information by allowing the patient's true urination patterns to be observed over a defined period of time, whether it be in a clinical setting, and/or at the patient's residence. The use of a device of the subject invention, in combination with recordation of the urination experience observations in a voiding diary, provide further insight to the patient's disease and symptoms, thus furthering diagnosis, and thereby, meaningful and effective treatment.

The endourethral prosthesis of the subject invention generally includes a tubular member positionable so as to traverse at least a portion of a prostatic urethra such that a portion of the tubular member is receivable within the bladder and adapted to receive and pass fluid therethrough. A reversibly expandable element is disposed circumferentially about, and longitudinally along the tubular member. The expandable element is operatively engagable so as to non-reversibly receive fluid passed through at least a portion of the tubular member, and thereby volumetrically expand for anchoring the portion of the tubular member receivable within the bladder. The reversibly expandable element is further operatively engagable so as to discharge the non-reversibly received fluid exterior to the tubular member.

The devices of the first four embodiments provide reduce PVR (i.e., facilitate bladder voiding), and allow increased urine flow rates in patients with obstructed urethras due to, for example, an enlarged prostate, if the prostate is the sole factor as it often is. These devices support or stent the prostatic urethra to allow relatively normal function of the external sphincter (i.e., at least a portion of the device is physiologically responsive to the actions of the external sphincter).

The device of the fifth embodiment permits free (i.e., physiological) movement of the bladder outlet, often referred to as the internal sphincter or bladder neck, and the external sphincter, thus allowing relatively unrestricted passage of urine from the bladder to these locations while supporting the prostatic urethra. Deployment of the device of this embodiment permits urine to naturally exit the bladder, and flow through and past the supported prostatic urethra, for purposes of both patient care, and to gather additional diagnostic information in furtherance of determining whether prostatic hyperplasia is the cause of the LUTS.

The device of the sixth embodiment further disables the bladder outlet and the external sphincter from restricting urination by providing a conduit for flow through the interior of the urethra along the length of the external sphincter. With the devices of this embodiment, voluntary initiation of urination combined with urine flow rate becomes a meaningful indicator of the functionality of the bladder. This indicator is meaningful because when urination is initiated by the user by removing the penile clamp, the user has no immediate control of the initiation of flow. The urine pathway is open, and flow will initiate from the influence of gravity and the weight of the individuals body mass on the bladder. Without the muscular influence of the bladder during the micturition cycle the flow will be slow. When the patient desires to urinate, the flow rate will increase substantially over a free flow state if the bladder is functioning properly.

Each device embodiment of the subject invention, and attendant methods associated therewith, provide users having good bladder function with lower PVR, which will, in many instances, temporarily offer relief from nocturia, and reduce the risk of full urinary retention. The devices of the several embodiments provide the urologist with useful options in assessing and temporarily treating patients with LUTS, more particularly by providing a highly effective, easily deployed device which permits differential diagnosis of subjects presenting with LUTS symptoms.

The foregoing and other objects, features, and advantages of the invention will be apparent with reference to the figures, the DETAILED DESCRIPTION OF THE INVENTION, and the claims herein after. The figures are not necessarily to dimensional or geometric scale, nor do they necessarily represent structures in accurate or representative relative scale. Emphasis rather is placed upon illustrating principals of the invention in a clear manner.

BRIEF DESCRIPTION OF THE DRAWINGS

FIG. 1 is a longitudinal sectional view of the device of the first embodiment of the subject invention, the anchoring feature shown activated;

FIG. 2 is a longitudinal sectional view of the device of the second embodiment of the subject invention, the anchoring feature shown activated;

FIG. 2A is an enlarged view of area 2A of the device of FIG. 2;

FIG. 3 is a longitudinal sectional view of the device of the third embodiment of the subject invention, the anchoring feature shown activated;

FIG. 3A is an enlarged view of area 3A of the device of FIG. 3;

FIG. 5 is a longitudinal partial sectional view of the insertion tool of the assembly of the subject invention;

FIG. 5A is a sectional view of the insertion tool of the assembly taken along line 5A–5A' of FIG. 5;

FIG. 6A is an enlarged view of area 6A of the assembly of FIG. 6, more particularly illustrating the cooperative engagement of the insertion tool and the device;

DETAILED DESCRIPTION OF THE DRAWINGS

The endourethral device of the subject invention, in all embodiments as well as with the assemblies and methods associated with the subject invention, are predicated on the notion of easy, secure, stable placement within the male urethra. The device embodiments subsequently discussed, whether they co-act and interact minimally with the structures of the lower urinary tract (e.g., include structures and relationships as discussed relative to the embodiment of FIG. 1), or more aggressively supplant the physiological workings of the anatomy thereof (e.g., include structures and relationships as discussed relative to the embodiment of FIG. 10), utilize an anchoring mechanism which is easily and reliably selectively actuable, and which further does not contribute to an overall cumbersome, heavy walled device shunned by those requiring such device for improved life quality.

Common to all endourethral device embodiments of the subject invention is a reversibly expandable element disposed circumferentially about, and longitudinally along a tubular member adapted to receive urine, the tubular member being positionable within a lower urinary tract such that the reversibly expandable element operatively engages a structure of the lower urinary tract so as to prevent migration of said prosthesis so positioned. The reversibly expandable element is in non-reversible fluid communication with the tubular element for selective expansion thereof, the reversibly expandable element further being operatively engagable so as to discharge fluid non-reversibly received from said tubular member exterior to the tubular member.

Figure 10:
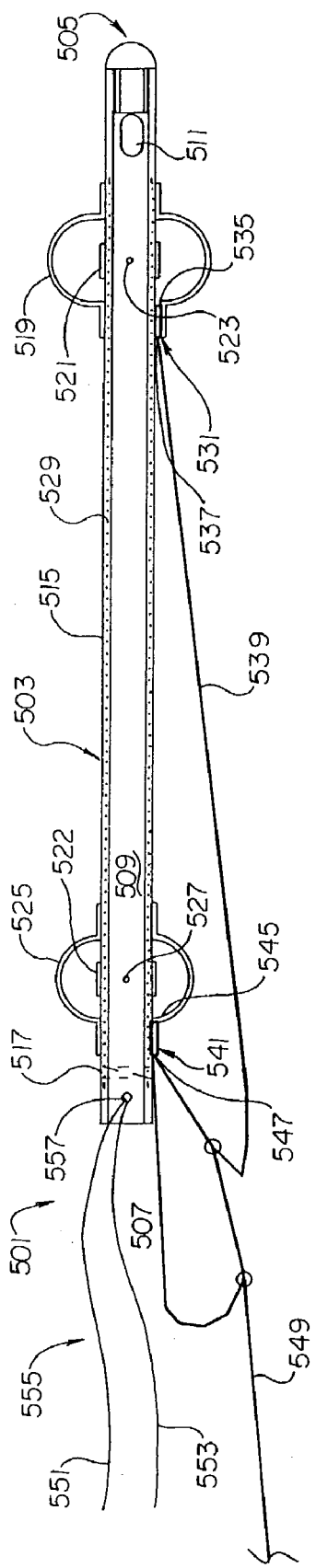
FIG. 10 is a longitudinal sectional view of the device of the sixth embodiment of the subject invention, the anchoring feature shown activated.

In the device embodiments of FIGS. 1–4 and 8, one and two sphincters respectively interact with the endourethral device to cooperate with the natural functions of the urinary tract so as to facilitate emptying of the bladder. The device embodiment of FIG. 10 is used in cooperation with an external collection system, or more preferably with a penile clamp as this device passes through the interior of both the internal and external sphincter, as well as through the prostatic urethra, thereby rendering the urinary passageway open. The device embodiment of FIG. 11 incorporates integral flow control means. Finally, the preferred assembly for treating urinary retention/aiding differential diagnosis of LUTS are presented in FIGS. 6–7.

Referring now to the figures, FIG. 1 illustrates the endourethral device 20 of the first embodiment in longitudinal sectional view. The device 20 generally includes an elongate tubular member 22 positionable for communication with a bladder, a reversibly expandable element 24 disposed circumferentially about, and longitudinally along the elongate member 22, and a fluid flow regulator 26 interposed between a fluid filling port 28 of the elongate tubular member 22 and the reversibly expandable element 24.

The elongate tubular member 22 generally has a wall 30, opposing first 32 and second 34 ends, and a lumen 36. The wall 30 extends between the opposing first 32 and second 34 ends of the member 22 and includes at least one fluid filling port 28 therein, or therethrough, as the case may be. As radial firmness of the wall is essential to accomplish a stenting function, the materials of construction, aside from the known compatibility issues, should thus exhibit same. It may be desirable to fortify the elongate tubular element vis-a-vis the use (e.g., integration of) a structural support coil 38 (i.e., the elongate tubular member may be axially reinforced so as to perform the sought after stenting function). The first end 32 of the elongate tubular member 22 preferably includes at least one urine receiving orifice 40, however plural apertures, or alternate urine ingress means are likewise contemplated and considered to be well within the skill of the subject art, and an end cap 42. The second end 34 of the elongate member 22 is designated as an "open" end (i.e., permits fluid flow egress), with the lumen 36 effectively joining or linking the at least one urine receiving orifice 40 with the second end 34 of the elongate member 22.

The reversibly expandable element 24, disposed about and along the elongate tubular member 22, overlays the at least one fluid filling port 28 in the wall 30 of the elongate tubular member 22. The reversibly expandable element 24 is operatively engagable, preferably by an insertion tool, as will later be detailed with respect to the tool and assembly disclosure associated with FIGS. 5–6A, so as to expand and thereby anchor the elongate tubular member with a lower urinary tract.

The fluid flow regulator 26 (i.e., valve), interposed between the at least one fluid filling port 28 and the reversibly expandable element 24, regulates the non-reversible fluid flow to the reversibly expandable element. More particularly, the fluid flow regulator 26 performs a "gate keeper" function, namely that of permitting the selective, one-way passage of fluid 44 into the reversibly expandable element 24. Preferably, but not necessarily, the fluid flow regulator 26 comprises a resiliently deformable band which is circumferentially disposed about the elongate tubular member 22 in the vicinity of the fluid filling port 28 so as to selectively overlay same in sealing engagement (i.e., ample filling pressure is imparted to the fluid 44 for introduction into the reversibly expandable element 24 so as to overcome the sealing effect of the fluid flow regulator 26).

Fluid 44 passing through the fluid filling port 28 (e.g., plurality of radial apertures) is received within the reversibly expandable element 24 in furtherance of reliably anchoring the elongate tubular member 22 (i.e., expanding the expandable element 24). The reversibly expandable element 24 is further operatively engagable so as to permit the selective discharge of retained or accumulated fluid from a fluid discharge channel 46 which traverses a wall 48 of the reversibly expandable element 24. The discharge or drainage of the retained fluid from the fluid discharge channel 46 is exterior to the elongate tubular element 22, thereby eliminating a further fluid passageway or lumen from the structure for such purpose, or achieving such functionality.

Preferably, the device 20 of the first embodiment (i.e., the base upon which further embodiments are built upon) further includes a plug 50 receivable in the fluid discharge channel 46. The plug 50, which is frictionally or otherwise received within an orifice 52 of the fluid discharge channel 46, is retained (e.g., affixed) upon a tether 54 for selective remote manipulation. The tether 54, as shown, comprises a lead 56, a plug segment or branch 58, a elongate tubular member segment or branch 60 which is secured to the open end 34 thereof, and a union point 64 for the branches. As will be later discussed, the lead portion 56 of the tether 54, which is capable of direct manipulation by external action, is implicated for device removal or repositioning, as the case may be. With a retrieval force applied to the lead 56 (i.e., to the left margin in FIG. 1), the plug 50 first exits the orifice 52 of the channel 46 to drain the reversibly expandable element 24, and while further tension is applied in taking up slack in the tether 54, the device 20, no longer anchored to urinary tract structures, is free to pass for exit from the urethra.

The device of this embodiment incorporates the useful features of proximal anchoring and prostatic urethra support while eliminating habitation of the device in the sphincteric and bulbous urethra. The device of this embodiment is stabilized from bladder migration by the pressure of the prostatic urethra engaging the external surface of the distal segment of device body. The device body may be selectively open to allow free urine and mucosal fluid mixing. It will be readily appreciated that in the contemplated assembly of the subject invention (i.e., the combination of the endourethral prosthesis with an insertion tool), a preferred insertion tool for use in an assembly for treating urinary retention/differentially diagnosing LUTS using the device of this embodiment requires modification from that later disclosed, such modification considered to be within the skill of those in the art (i.e., the insertion tool receiving this device in an assembly requires only one inflation passageway, and one pair of sealing rings, as is readily appreciated upon review of the subsequent description of the insertion device-apparatus interface).

The preferred materials for the device of this and the several embodiments include, but are not limited to: Silbione 40029 silicone rubber (30A Durometer, per ISO 10993-1 and FDA guidelines) for the device body, end cap, and coated surfaces; Nusil Technology MED1-4213 implant grade adhesive for expandable element and cap bonding to the tubular element, as well as for encapsulation. It is further noted that 304 stainless steel is desirably used for fabrication the device body, or portions thereof, and at a minimum is advantageous for its stress/strain quality so as to function as a reinforcing member in the device. Tethers comprise suture materials of silk, or silicone coated silk from Ashaway Line & Twine, and are USP-VI.

Figure 4:
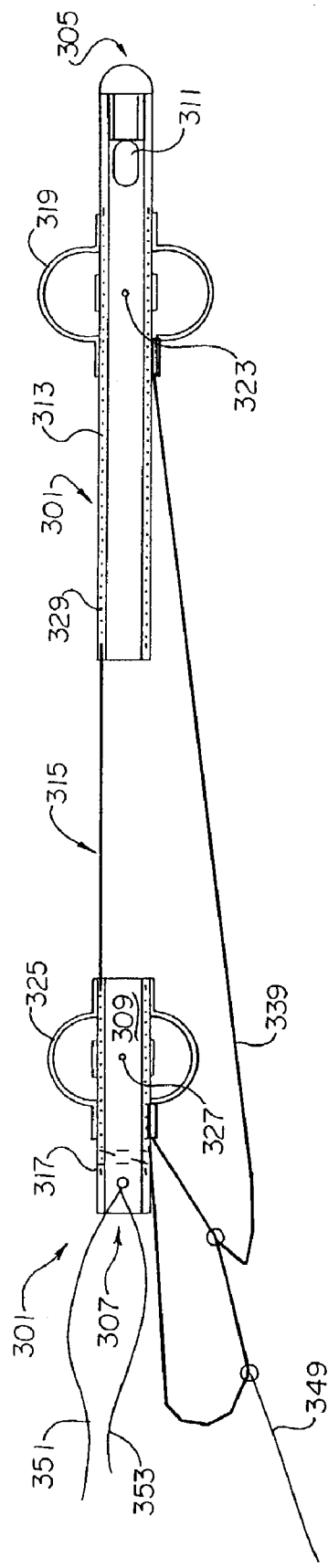
FIG. 4 is a longitudinal sectional view of the device of the fourth embodiment of the subject invention, the anchoring feature shown activated.

Building on the FIG. 1 embodiment, the device embodiments of FIGS. 2–4 might be fairly said to be a variation on a theme. More particularly, the devices of FIGS. 2–4 further include a second tubular element positionable within a bulbar portion of the urethra, the second tubular element being indirectly joined to said first tubular member (e.g., as by a sphincter responsive linkage extending between the elongate tubular members and adapted to receive and pass urine therethrough. The second tubular element, as the first, includes a second reversibly expandable element disposed thereabout, and longitudinally there along, the reversibly expandable element overlaying at least one fluid filling port in a wall of the second elongated tubular member. Again, as first reversibly expandible element, the second reversibly expandable element is operatively engagable so as to expand and thereby anchor the second elongate tubular member within a lower urinary tract.

As will be subsequently detailed, the sphincter responsive linkage of the device of FIG. 2 includes a conduit for receiving urine from the first elongate tubular member and discharging same to the second elongate tubular member, the conduit being reversibly collapsible, and preferably adapted to receive glandular fluids physiologically introduced into the urethra; the sphincter responsive linkage of the device of FIG. 3 includes a partially open channel for receiving and passing urine therethrough; and finally, the sphincter responsive linkage of the device of FIG. 4 takes the form of a joining wire or coil, more particularly, but not necessarily, the wire is an "exposed" portion of a supplemental structural support element used to enhance radial firmness of the first and second elongated tubular members (i.e., the joining wire or coil extends to effectively traverse the ends of the device).

Referring generally to FIGS. 2 & 2A, the endourethral device 101 of the second embodiment is shown in longitudinal sectional view. The endourethral device 101 generally includes a elongate device body 103 having proximal 105 and distal 107 extremities. A fluid passageway or lumen 109 longitudinally extends through device body 103, from at least a single urine receiving orifice 111, to the distal extremity 107 thereof. The device body 103 includes, in sequential alignment, a proximal portion 113, a central portion 115, and a distal portion 117, each portion thereof being segued transitions of the device body 103. The central portion 115 is preferably relatively thin walled, and is easily, and reversibly collapsible (i.e., resilient) by external forces, more particularly, as will later be explained in detail, this central portion 115 is said to be physiologically responsive to the adjacent urinary tract structures when operably deployed.

A proximal balloon 119, disposed circumferentially around and longitudinally along the proximal portion 113 of the device body 103, is preferably attached by silicone adhesive, more particularly, a silicone adhesive from NuSil Technology (MED1-4213). To assist in bond adhesion, it is further preferred that NuSil Technology primer coat (material CF2-135) be applied. Band seal 121 is shown covering filling orifice 123 with both located beneath proximal balloon 119. Distal balloon 125 is shown located on the exterior of the distal elongate member 117. Band seal 122 is shown covering filling orifice 127. Proximal elongate member 113 and distal elongate member 117 maintain enhanced radial firmness, preferably but not necessarily with the structural support of coil 129.

Balloon plug 131 is positioned in relief passage 133, such that the proximal end 135 terminates within proximal balloon 119, and the distal end 137 is attached to balloon tether 139 which extends distally beyond distal extremity 107. Distal balloon plug 141 is positioned within relief passage 143, such that the proximal end 145 terminates within distal balloon 125, and the distal end 147 is attached to balloon tether 149 which extends distally beyond distal extremity 107.

First strand 151 and second strand 153 of tension tether 155 extend distally from eyelet 157. The strands function in cooperation with the insertion tool of FIG. 5 to maintain tension on the urethral device during insertion.

Referring particularly to FIG. 2A, an expanded partial sectional view illustrates the central elongate member 115. One, multiple, or a plurality of holes 159 in a pattern may extend so as to establish communication between the interior and the exterior of central elongate member 115. The function of these communicative pathways is to allow fluids secreted by the prostate, the bulbourethral gland, and the urethral glands which are located along the entire length of the urethra to drain, thus not entrapping the fluids between the urethral device and the urethra. These glands secrete fluids evolved during sexual activities, and also are thought to contribute an inhibitory response against bacterial infection.

Referring generally to FIGS. 3 & 3A, the device of the third embodiment is shown in longitudinal perspective view. Urethral device 201 is identical to the device 101 with the exception of the emission of material from the device body 203 in the central elongate member 215 corresponding to elongate member 115 (FIG. 2). Omission of the material allows for a smaller surface area for the external sphincter to compress, and better release of urine which may flow external of the central elongate member 215 and allowing it to pass through the interior of distal elongate member 217.

Figure 4A:
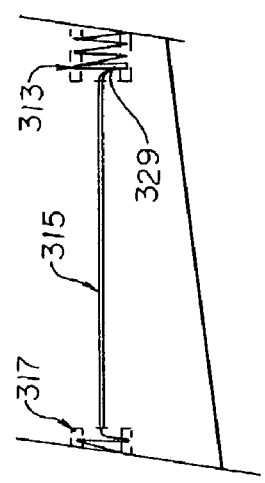
FIG. 4A is an enlarged view of area 4A of the device of FIG. 3.

Referring generally to FIGS. 4 & 4A, the device 301 of the third embodiment is shown in longitudinal sectional view. Urethral device 301 is similar to the device 101 with the exception of the emission of material in the central elongate member 315. Structural body 301 is coated with silicone to provide interior surfaces beneath proximal balloon 319 and distal balloon 325. The coating is selectively applied to the remaining portions of the proximal elongate member 313 and distal elongate member 317 and continues from proximal extremity 305 to distal extremity 307. All external surfaces are preferably silicone. The preferential application of the silicone selectively allows for the secretions from the mucosal glands within the prostatic urethra to pass and mix with the urine in the prostatic urethra.

Prior to a detailed discussion of the insertion tool (FIGS. 5 & 5A) of the assembly (FIGS. 6 & 6A) of the subject invention, a few remarks and or observations about the assembly are helpful at this point. The assembly, which is suited for therapeutic or diagnostic uses, generally includes an endourethral device of the subject invention, in combination with an insertion tool for deploying said endourethral device in a lower urinary tract. The insertion tool preferably includes an elongate body having opposing first and second ends, a wall traversing the opposing ends, and a device receiving portion longitudinally extending from the first end of said elongate body. The device receiving portion is generally adapted to pass fluid from a fluid passageway longitudinally extending from the second end of the body to the reversibly expandable element of the device, in furtherance of anchoring said elongate tubular member within the lower urinary tract.

Referring generally to FIGS. 5 & 5A, insertion tool 900 is shown in a longitudinal section view. Insertion tool 900 is described along the longitudinal axis from the proximal extremity 922 to distal extremity 924. Proximal sealing ring 932 is located near the proximal extremity 922. Proximal fill orifice 940 enters interior of elongate member 928 into passageway 950 which terminates at proximal fill luer fitting 910. Second proximal sealing ring 934 is located distal of proximal fill orifice 940. Proximal sealing ring 932 and second proximal sealing ring 934 are positioned approximately 1 centimeter apart. Progressing along the longitudinal axis approximately 5 centimeters in the distal direction, the next protruding feature is the first distal sealing ring 936. Distal filling orifice 942 is located distal of sealing ring 936, and proximal of second distal sealing ring 938. Proximal fill orifice 942 enters passageway 952 terminates at the distal fill luer fitting 920. Elongate member 928 enters silicone tube 926 approximately 3 centimeters from second distal seal 938. Silicone tube 926 has proximal extremity 929, and distal extremity 924. Near the distal extremity 924 of silicone tube 926, bifurcation occurs between passageway 950 and passageway 952 in the elongate member 928.

Referring especially to FIG. 5A, support rod 954 extends from proximal extremity 922 of the insertion tool, through interior of passageway 950 to a location near luer fitting 910. Support rod 954 may be optionally formed into a slight curvature to provide a curvature of multi-lumen tube which comprises elongate member 928 proximal of proximal sealing ring 932. This curvature biases causes a similar curvature of the end of the urethral device. This feature is useful for select patients where curvature of the urethra prohibits introduction of the device. Similar curvatures are incorporated in the tips urinary catheters (i.e., "coude" tips).

Figure 6:
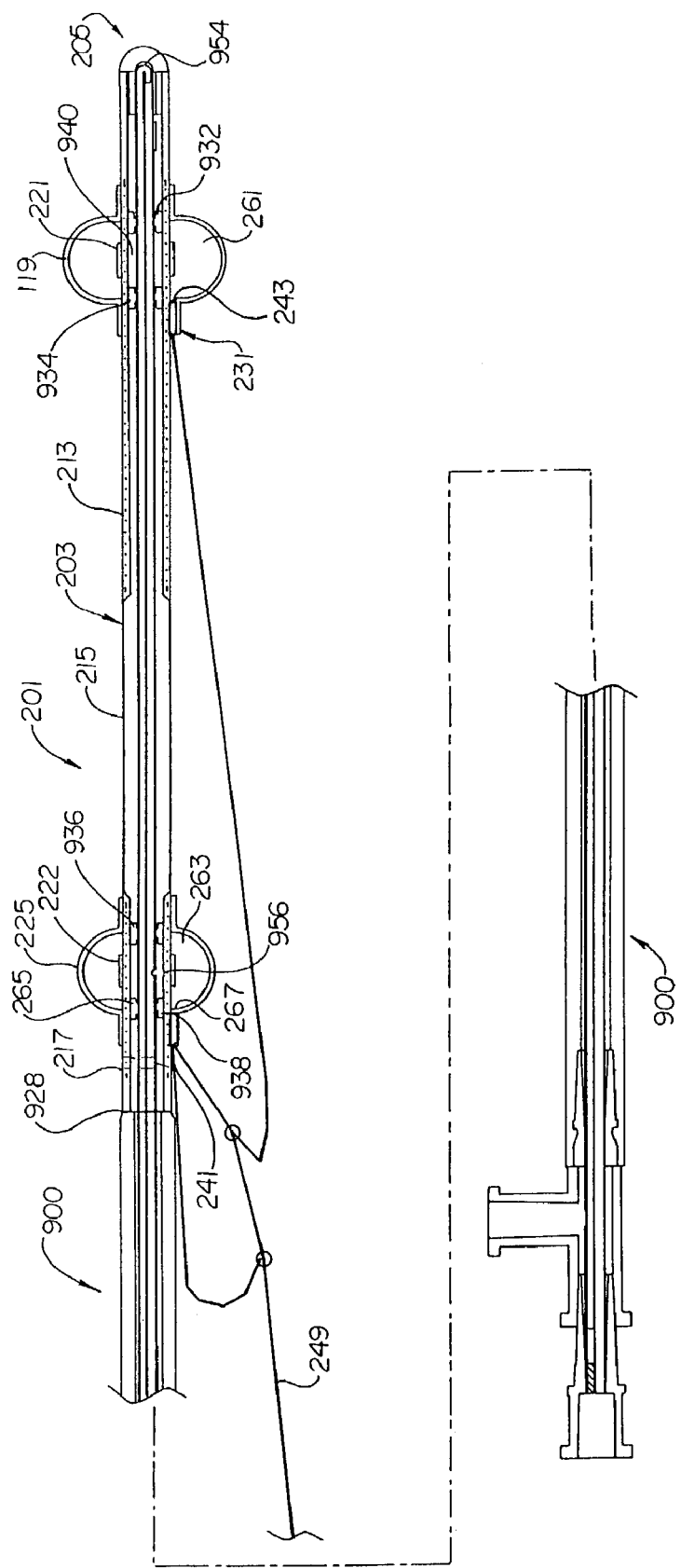
FIG. 6 is a longitudinal sectional view of an assembly of the subject invention, more particularly, the device of FIG. 2 is shown operatively engaged with the insertion tool of FIG. 5, the anchoring feature of the device shown activated.
Figure 7:
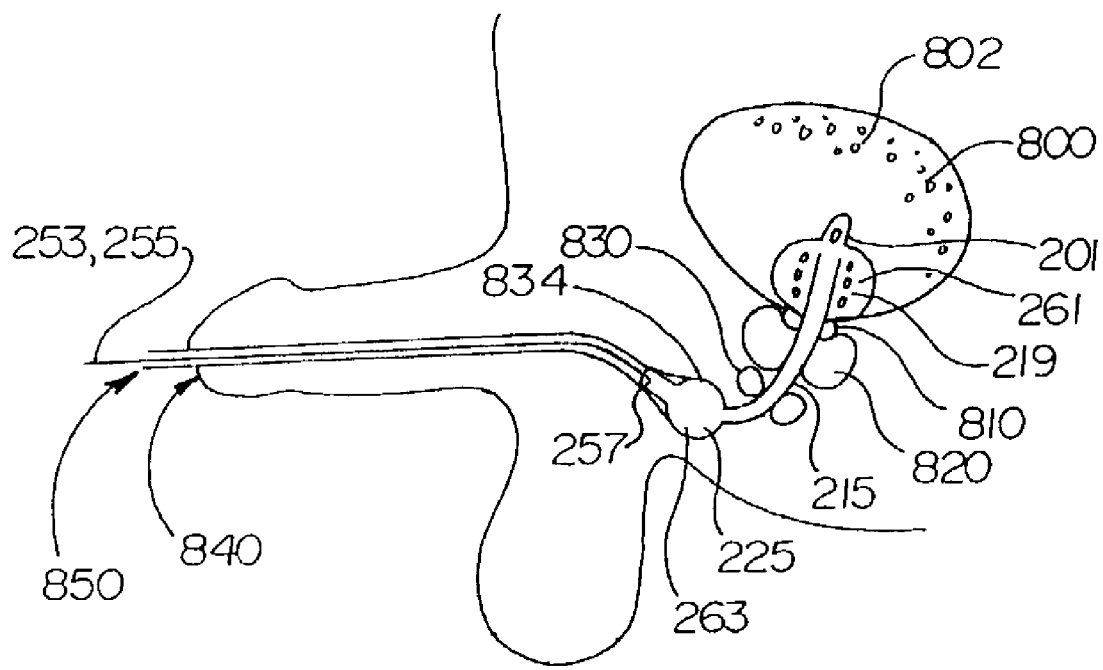
FIG. 7 is a artistic illustration of the device of FIG. 2 in-situ within the male bladder and urinary tract.

Referring generally to the assembly of FIGS. 6 & 6A, and the deployed device of FIG. 7, insertion tool 900 is illustrated when positioned within urethral device 201 (embodiment of FIG. 2). Prior to filling of proximal balloon 219, and distal balloon 225, the balloons lay flat on the perimeter of the proximal elongate member 213 and distal elongate member 217 respectively.

After urethral device 201 has been inserted into penile urethra 850 it is gently pushed towards the bladder 800 by insertion tool 900. When sufficient length has been introduced, proximal balloon 219 is expanded by the introduction of fluid 261 into proximal fill luer fitting 910. Fluid 261 passes through interior of passageway 950 (FIG. 5A) along axis of insertion tool 900 until it passes through proximal fill orifice 940. First and second proximal sealing rings 932 and 934 respectively seal against proximal interior surface 980. Fluid 261 then passes through proximal orifice 223 past band seal 221. Flow arrow 960 illustrates the fluid flow pathway. Band seal 221 acts as a one way valve allowing only limited resistance to fluid flow into proximal balloon 219, while prohibiting the return of same. Prior to filling proximal balloon 219, it is filled according to the physician's assessment of the requirements for the user's bladder, with an average volume of approximately 5 cc being typical.

Following the filling of proximal balloon 219, the assembly is gently pulled distally by placing tension on tether segments 151 and 153 of tether 155 (FIG. 7) which are looped through eyelet 157 of the urethral device 201. When the health care giver experiences a slight tension on tensioning tethers, they will know that the distal surface of balloon 219 is gently pressing against bladder neck 806. This is the intended location for the device. The distal balloon 225 is then inflated in the bulbar urethra 834.

Distal balloon 225 is then filled by the introduction of fluid 263 into distal fill luer fitting 920. Fluid 263 passes through interior of passageway 952 (FIG. 5A) along axis of insertion tool 900 until it passes through distal fill orifice 956. First and second distal sealing rings 936 and 938 respectively seal against distal interior surface 265. Fluid 263 then passes through distal orifice 956 past distal band seal 222. Distal band seal 222 acts as a one way valve allowing only limited resistance to fluid flow into distal balloon 225, while prohibiting the fluid's return balloon 225 it is filled according to the physicians assessment of the requirements for the users bladder, with an average fill volume being about 3 cc. When properly placed, balloon 225 is contained within the bulbous urethra 834.

Once the physician or care giver is satisfied that urethral device is properly positioned, the insertion tool 900 is removed. Removable tensioning tethers 251 and 253 form a single loop which is released by releasing either from retainer 972 (FIG. 5). By gently pulling on first tether length 251, the second tether length 253 is free to draw towards proximally towards eyelet 257. When the care giver continues to pull the first length 252, the entire tensioning tether may be withdrawn from the patient. Insertion tool 900 will then freely uncouple from the urethral device 201. Withdrawal of insertion tool 900 is a free (i.e., unencumbered) process. The sealing mechanism between the sealing rings 932, 934, 936 and 938 is enabled by an interference fit of approximately 0.009 inches with the interior of the device body 203 at in the balloon regions. Thus, the device is securingly deployed with the distal balloon tether 249 extending distally to either extend out of the penis, or alternatively terminate within the distal penile urethra 850.

Urethral device 201 is easily removed by the following method which demonstrates further useful features of the devices of the several embodiments. Urethral device 201 is equipped with a removable proximal plug 231 and distal plug 241 to release the fluid 261 from the proximal balloon 219, and distal balloon 225. Proximal plug 231 is placed in relief passage 243 which, when unplugged, provides a fluid passageway between interior of proximal balloon 219, and the exterior of urethral device 201 for flow into the bladder 800. Similarly, distal plug 241 is placed in passage 167. Distal plug 241 is interconnected with distal balloon tether 239.

As to the removal sequence, a care giver first drains the distal balloon 225 by pulling distal balloon tether 239. This is accomplished by gently placing tension on distal balloon tether 239 either by grasping the section which extends from the penis, or by the device and method described in co-pending application Ser. No. 09/724,239, entitled MAGNETIC RETRIEVAL DEVICE & METHOD OF USE, the entire disclosure of which is incorporated herein by reference.

After tension is felt, as by gently continuing to draw the balloon tether 239 outwardly, distal balloon plug 241 will be withdrawn from relief passage 267. When relief passage 267 is opened, the fluid 263 passes into bulbous urethra 834, and subsequently exits the body. Distal balloon tether 239 is affixed to proximal balloon tether 249. When the care giver continues to draw balloon tether 239 outwardly, the slack will be taken out of proximal balloon tether 249, and proximal balloon plug 232 will be withdrawn from relief passage 243. When relief passage 233 is opened, the fluid 261 will empty into bladder 800, and mix with any residual urine which is present. After removal of the proximal balloon plug 231, the care giver will wait approximately 1 minute. This will assure complete draining of both of the balloons. Continued gentle withdrawal of the distal balloon tether 249 will be used to pull the urethral device 201 from the user.

Figure 8:
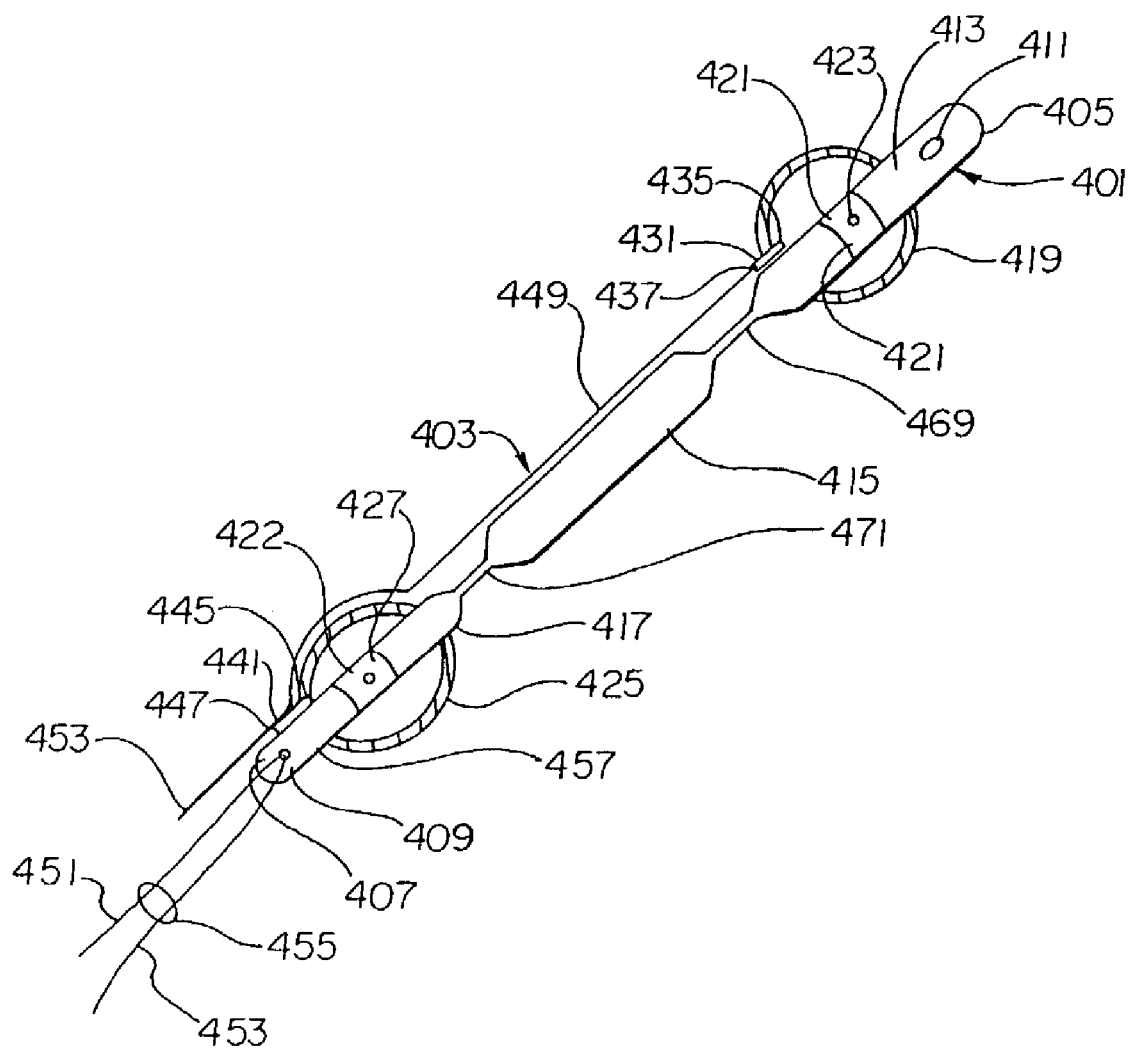
FIG. 8 is a perspective view of the device of the fifth embodiment of the subject invention, the anchoring feature shown activated.

Returning again to a detailed discussion of the several embodiments, and referring now to FIG. 8, the device of the fifth embodiment is shown in a perspective longitudinal section view. This device is configured to accommodate the natural physiological function of both the bladder outlet (internal sphincter), and the external sphincter while supporting the prostatic urethra. Urethral device 401 consists of a continues device body 403 with a proximal extremity 405 and a distal extremity 407. A passageway 409 extends through the interior of urethral device 401 from orifice 411 to the distal extremity 407. The passageway 409 extends through the interior of proximal elongate member 413 with segued transitions to first placid elongate member 469, central elongate member 415, second placid elongate member 471, and distal elongate member 417. Both first placid elongate member 469, and second placid elongate member 471 are relatively thin walled, and easily collapsible by external forces and may optionally have a portion of the material absent as in the second, third and fourth embodiments previously discussed.

Proximal balloon 419 encapsulates band seal 421 and orifice 423. Band seal 421 is shown covering filling orifice 423 with both located beneath proximal balloon 419. Distal balloon 425 is shown located on the exterior of the distal elongate member 417. Band seal 422 is shown covering filling orifice 427.

Balloon plug 431 is positioned such that the proximal end 435 terminates within proximal balloon 419, and the distal end 437 is attached to balloon tether 449 which extends distally beyond distal extremity 407. Distal balloon plug 441 is positioned such that the proximal end 445 terminates within distal balloon 425, and the distal end 447 is attached to balloon tether 453 which extends distally beyond distal extremity 407.

First strand 451 and second strand 453 of tensioning tether 455 extend distally from eyelet 457. Tensioning tether 455 functions in cooperation with the insertion tool 900 shown in FIG. 5 to maintain tension thereon during insertion. Insertion and removal of urethral device 401 is conducted in the same manner as previously described for the several embodiments.

Figure 9:
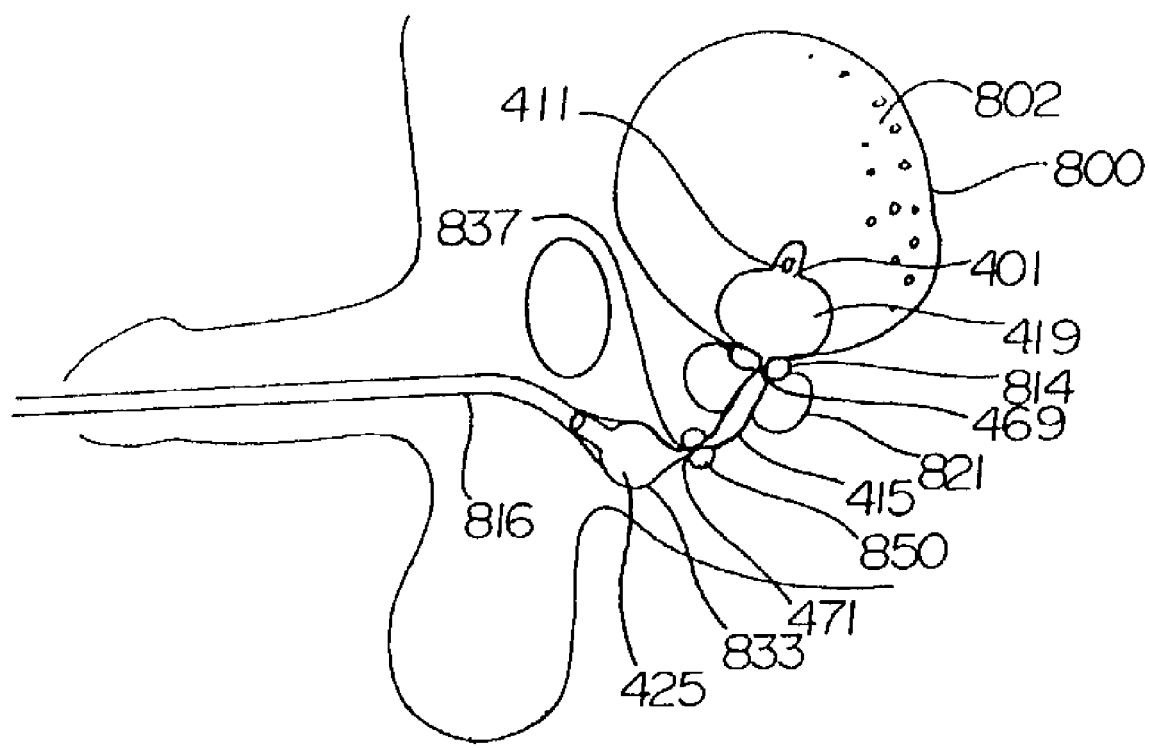
FIG. 9 is an artistic illustration of the device of FIG. 8 in-situ with in the male bladder and urinary tract.

FIG. 9 is an artistic illustration of the device of FIG. 8 in-situ with in the male bladder and urinary tract.

Urethral device 401 is located within bladder 800 having urine present within thereon. The proximal balloon 419 is shown located proximally of the internal sphincter 814. The internal sphincter 814 encapsulates and compresses urethra 816 which subsequently compresses first placid elongate member 469. Prostate gland 821 also encapsulates urethra 816. When the prostate gland 821 is enlarged, as often occurs with aging, it may also compress the urethra 816. Central elongate member 415 is positioned within the interior of the length of encapsulation of the prostate gland 821. Central elongate member 415 is of sufficient radial stiffness that the prostate gland 821 will not collapse it. The external sphincter 850 is located distally of the prostatic urethra, and slightly anterior. The external sphincter 850 also encapsulates and the urethra 816. The second placid elongate member 471 is located directly interior of the external sphincter 850. Distal balloon 425 is positioned within the bulbous urethra 833. Urine is released from bladder 800 by the natural micturition process. The internal sphincter 814, and the external sphincter 850 withdraw the urethra 816. Simultaneously the bladder 800 contracts forcing urine from the bladder 800. When internal sphincter 814, and external sphincter 850 dilate, the first placid elongate member 469, and second placid elongate member 471 dilate due to the internal pressure of the urine. Urine exits the body by entering orifice 411 of urethral device 401, and passes through the interior passageway 409, and exits the distal extremity 407 into the urethra 816. It may be easily appreciated that if either the internal sphincter 814, or the external sphincter 850 fail to either release or compress urethra 816, the patient will not experience a normal emptying of the bladder. This illustrates the usefulness in understanding bladder and sphincter functions.

Referring now to FIG. 10, the device of the sixth embodiment is shown in longitudinal sectional view. Urethral device 501 consists of a continuous device body 503 with a proximal extremity 505 and a distal extremity 507. A passageway 509 extends through the interior of urethral device 501 from orifice 511 to the distal extremity 507.

Proximal balloon 519 is located proximally from orifice 511 on the outer surface. Band seal 521 covers filling orifice 523 with both located beneath proximal balloon 519. Distal balloon 525 is located on the distal exterior of elongate member 503. Band seal 522 covers filling orifice 527 with both located beneath filling orifice 527.

Balloon plug 531 is positioned such that the proximal end 535 terminates within proximal balloon 519, and the distal end 537 is attached to balloon tether 539 which extends distally beyond distal extremity 507. Distal balloon plug 541 is positioned such that the proximal end 545 terminates within distal balloon 525, and the distal end 547 is attached to balloon tether 549 which extends distally beyond distal extremity 507.

First length 551 and second length 553 of tensioning tether 555 extend distally from eyelet 557. Tensioning tether 555 functions in cooperation with the insertion tool 900 shown in FIG. 5 to maintain tension on the urethral device 501 during insertion.

The insertion and removal method and sequence for urethral device 501 is performed in like manner as with prior device embodiments. When urethral device 501 is in-situ within the urinary tract, the urine may freely drain from the bladder because the function of the external sphincter has been circumvented by being "stented" open. Urine drainage may than be controlled by a penile clamp. Alternatively, urine may be collected by a external collection device which is attached to an external condom catheter. When the urination process is performed for urodynamic assessment, the bladder strength may be easily observed due to the lack of potential for inhibition of flow from the bladder outlet, prostatic urethra or external sphincter. A weak flow will strongly imply weak bladder function, while the converse is true for a strong flow.

Figure 11:
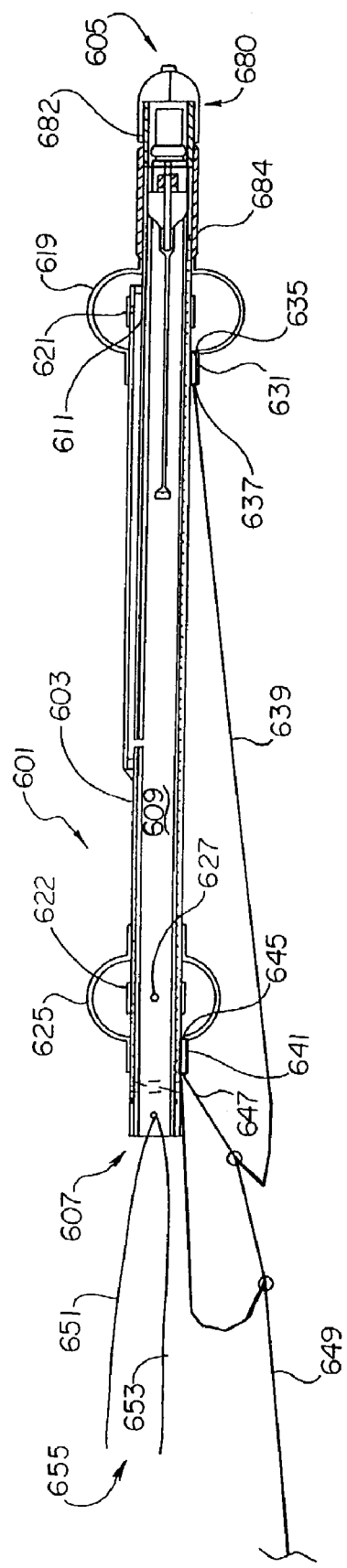
FIG. 11 is a longitudinal sectional view of the device of the seventh embodiment of the subject invention, the anchoring feature shown activated; and, FIG. 12 is an artistic illustration of the device of FIG. 11 in-situ within the male bladder and urinary tract.
Figure 12:
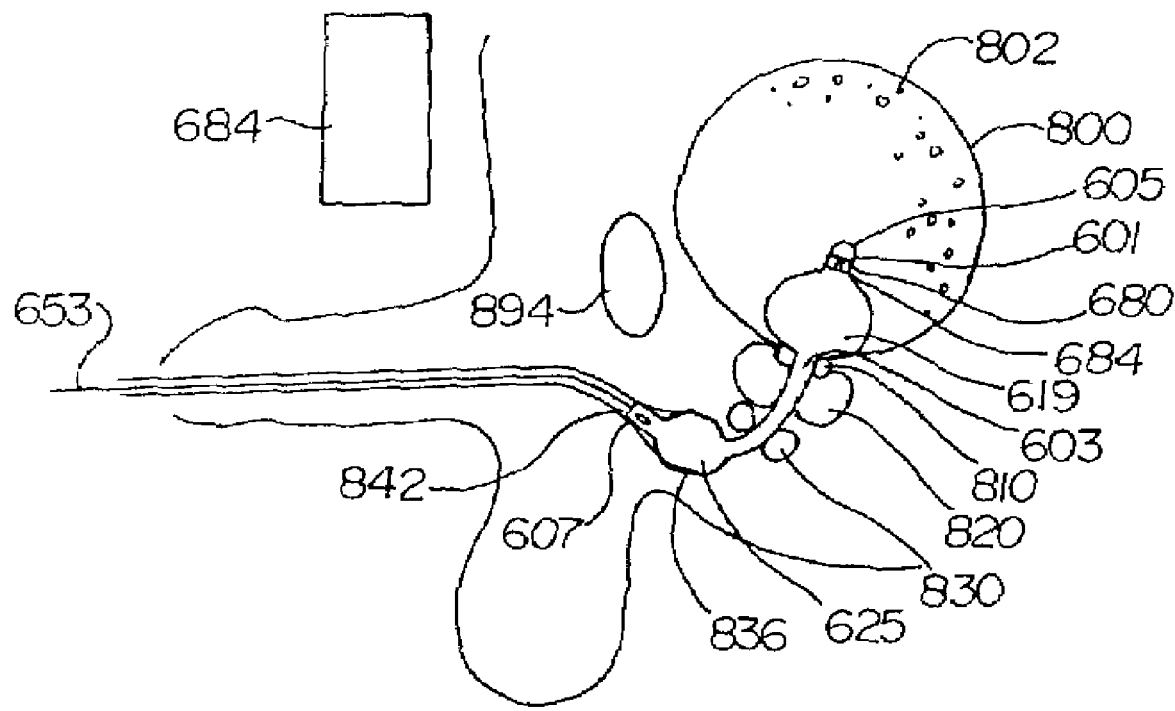

Referring to FIGS. 11 & 12, endourethral device 601 includes a continuous device body 603 with a proximal extremity 605 and a distal extremity 607. The device of this embodiment differs from the devices of the other embodiments by the presence of a flow control module 680 near the proximal extremity 605. The flow control module 680 is the subject of co-pending patent application Ser. No. 09/772, 088, entitled URINARY FLOW CONTROL DEVICE AND METHOD, the entire disclosure of which is incorporated herein by reference.

The flow control module 680 is located at this proximal location so that when the device is in-situ, the flow control module is positioned in the bladder. This location is chosen so that flow rates of urine may be maximized. This maximization occurs due to the elements of the flow control module 680 being located proximally of urine flow port 682 within flow control casing 684, and having minimal contact with the flow of urine during urination. Urine generally flows tangentially to the elements of the urine control module 680 when properly deployed. A passageway 609 extends through the interior of urethral device 601 from proximal port 682 to the distal extremity 607. The passageway 609 extends through the interior of device body 603.

Proximal balloon 619 is shown located proximally from orifice 611 on the outer surface. In similar manner as with previous embodiments, device is filled with the cooperation of a band seal 621 is shown covering filling orifice 623 with both located beneath proximal balloon 619. Distal balloon 625 is shown located on the distal exterior of elongate member 603. Band seal 622 is shown covering filling orifice 627.

The insertion and removal method and sequence for urethral device 601 is performed in a like manner, and consistent with that of the previously discussed device embodiments. Proximal balloon plug 631 is positioned such that the proximal end 635 terminates within proximal balloon 619, and the distal end 637 is attached to balloon tether 639 which extends distally beyond distal extremity 607. Distal balloon plug 641 is positioned such that the proximal end 645 terminates within distal balloon 625, and the distal end 647 is attached to balloon tether 649 which extends distally beyond distal extremity 607.

First length 651 and second length 653 extend distally from eyelet 657. Tether 655 in cooperation with the insertion tool 900 shown in FIG. 5 functions to maintain tension on the urethral device 601 during insertion.

Referring now particularly to FIG. 12, the device 601 is shown in an artistic rendering in-situ in the male urethral tract. Bladder 800 is shown filled with urine, with balloon 619 illustrated as being filled with fluid. The balloon is positioned in-situ near internal urethral sphincter 810. Distal from the urethral sphincter 810, the next anatomical component is prostate gland 820. Again, distal of the prostate gland 820 is the external sphincter 830. Distal again along the longitudinal axis, the distal balloon 625 is located in the bulbar urethra 836. The distal extremity 607 terminates in the urethra approximately 3 centimeters distally along the longitudinal axis from the external sphincter 830.

The flow control module 680 is initiated by introduction of magnet 684 to a position approximately adjacent to pubic bone 894. The magnet 684 is then magnetically linked to the internal components of control module 680. Flow is initiated by the pressure on the urine, and upon initiation of flow, urine empties from bladder entirely when flow control module 680 latches open, consistent with the device of the aforementioned co-pending application entitled URINARY FLOW CONTROL DEVICE AND METHOD. The initiation pressure is provided by the muscular action of the bladder 800 when stimulated by the nervous system.

The use of each of the embodiments requires a knowledge of the anatomical length from the bladder outlet to the exterior of the external sphincter. For the first five embodiments the length is more critical than for the sixth and seventh embodiments. The first five embodiments may not be excessively long or short, while the later require only that the are long enough.

The use of three lengths has been selected to serve the diverse patient population, with measurement of the lengths achieved either by cystoscopy, or by trans-rectal ultrasound, all routine clinical procedures. The lengths which are currently thought to be most suited to the population are indicated in the table hereinafter, with the equivalent outer diameters differing according to, or as a function of use. The preferred currently is a range of 18 to 24 French. With a center device with a 21 French exterior profile and an interior passageway of 12 French in the prostatic segment.

| Prostate Length Measurement (cm) | Size | Prostatic Stent Length (cm) | Balloon to balloon length (cm) |
|---|---|---|---|
| <3.0 | small | 3.0 | 5.4 |
| 3.1 to 4.2 | medium | 4.2 | 7.4 |
| 4.3 to 5.4 | large | 5.4 | 9.4 |

Measurement of the prostatic urethra without the use of cystoscopy or trans-rectal ultrasound is the subject of co-pending provisional application Ser. No. 60/299,973, entitled PROSTATIC URETHRA ADJUNCTIVE MEASUREMENT DEVICE AND METHOD OF USE THEREOF, filed Jun. 22, 2001, the contents of which are herein by incorporated by reference.

The useful features of the several embodiments of the subject invention may be appreciated by those of skill in the art, and by clinical care givers. All embodiments may be easily placed and stabilized within the male urethra. In the embodiments of FIGS. 1–5, one and two sphincters respectively interact with the urethral device to cooperate with the natural functions of the urinary tract to facilitate emptying of the bladder. The embodiment of FIG. 8 is used in cooperation with an external collection system, or more preferably with a penile clamp. The embodiment of FIG. 10 passes through the interior of both the internal and external sphincter, as well as through the prostatic urethra. This device renders the urinary passageway open. For BOO patients, restraining the sphincters and prostate from closing the urethra will provide for the patient's protection from obstruction, and from "obstructions" progressing to the point of urinary retention. Retention may be a dangerous clinical condition, since the urine may not pass from the bladder and one or more of the following physical difficulties may occur; discomfort or pain, stone formation, bladder infections, or kidney reflux.

The embodiment of FIG. 11 allows for the elimination of the external controls due to the proximally positioned magnetic flow module. Again, the internal sphincter, external sphincter and prostate are rendered open. Unlike previous embodiments, patients with sphincter dysfunctions such as sphincter dysnergia, hyper and hypo contractility, hyperactive bladders, and decompensated bladders may be accommodated. Two basic clinical parameters which will be improved by the use of the proper device are PVR, which provides information about the extent of emptying of the bladder, and urine discharge flow rate. In addition, these parameters will provide valuable information which is useful in the diagnosis of the patients needs. This is the case, because when a patient presents to the Urologist with difficulty urinating, the urologist may be unsure as to his complete condition which contributes to his difficulty. The urologist has the option of performing complex urodynamic evaluations, or providing him with a pharmaceutical, or clinical intervention directed towards relieving pressure on the urethra from the prostate. The patient may, however, be experiencing difficulty with his bladder function, or sphincter interactions. The following table illustrates how during the use of each of the several device embodiments information may be gathered which will provide the clinician, in a minimally invasive way, a more advanced understanding of the status of the patients urinary tract.

| Device Embodiment | Preliminary Post Void Residual | PVR with device | Preliminary Flow Rate | Flow Rate with Device | Possible Clinical Status BOO |
|---|---|---|---|---|---|
| First, second, third, fourth | high | low | low | high | Bph, int. sph. |
| First, second, third, fourth | high | low | low | low and app. equal | dcb, int sph, ext sph |
| First, second, third, fourth | high | high | low | low | ext sph. |
| Fifth | high | low | low | high | Bph |
| Fifth | high | low | low | low | dcb |
| Fifth | high | high | low | low | int./ext sphincter ab. |

-continued

| Device Embodiment | Preliminary Post Void Residual | PVR with device | Preliminary Flow Rate | Flow Rate with Device | Possible Clinical Status BOO |
|---|---|---|---|---|---|
| Sixth (clamp) | high | low | low | high | Bph, int./ext. sphincter ab. |
| Sixth | high | low | low | low | dcb, int./ext sphincter ab. |
| Seventh | high | low | low | high (***fcd comp) | Bph int./ext. sphinc. ab. |
| Seventh | high | low | low | high (***fcd comp) | dcb int./ext. sphinc. ab |

LEGEND:
BPH: Benign prostate hyperplasia (note: other testing is required to confirm that obstruction is benign)
dcb: Decompensated bladder
sphinc: sphincter
int: internal
ext: external
int/ext: internal and/or external

What is claimed is:

1. An endourethral device comprising:
   a. an elongate tubular member positionable for communication with a bladder, said elongate tubular member having a wall, opposing first and second ends, and a lumen, said wall extending between said opposing first and second ends, said first end having at least one urine receiving orifice, said second end being an open end, said lumen joining said at least one urine receiving orifice with said second end;
   b. a reversibly expandable element disposed circumferentially about, and longitudinally along said tubular member, said reversibly expandable element overlaying at least one fluid filling port in said wall of said elongated tubular member, said reversibly expandable element being operatively engageable so as to expand and thereby anchor said elongate tubular member within a lower urinary tract, said reversibly expandable element being further operatively engageable so as to permit selective discharge of retained fluid from a fluid discharge channel exterior of said elongate tubular member, said fluid discharge channel traversing a wall of said reversibly expandable element;
   c. a fluid flow regulator interposed between said at least one fluid filling port and said reversibly expandable element for regulating non-reversible fluid flow to said reversibly expandable element;
   d. a flow controller positionably supported within said lumen of said elongate tubular member by a bladder indwelling portion thereof; and,
   e. means for selectively permitting flow of retained fluid from said fluid discharge channel.

2. The device of claim 1 wherein said flow controller is adjacent said at least one urine receiving orifice.

3. An endourethral device comprising:
   a. an elongate tubular member positionable for communication with a bladder, said elongate tubular member having a wall, opposing first and second ends, and a lumen, said wall extending between said opposing first and second ends, said first end having at least one urine receiving orifice, said second end being an open end, said lumen joining said at least one urine receiving orifice with said second end;
   b. a reversibly expandable element disposed circumferentially about, and longitudinally along said tubular member, said reversibly expandable element overlaying at least one fluid filling port in said wall of said elongated tubular member, said reversibly expandable element being operatively engageable so as to expand and thereby anchor said elongate tubular member within a lower urinary tract, said reversibly expandable element being further operatively engageable so as to permit selective discharge of retained fluid from a fluid discharge channel exterior of said elongate tubular member, said fluid discharge channel traversing a wall of said reversibly expandable element;
   c. a fluid flow regulator interposed between said at least one fluid filling port and said reversibly expandable element for regulating non-reversible fluid flow to said reversibly expandable element; and,
   d. a plug receivable in said fluid discharge channel, said plug being retained upon a tether for selective remote manipulation.

4. The device of claim 3 wherein said plug sealingly engages an orifice of said fluid discharge channel.

5. The device of claim 4 wherein said fluid flow regulator comprises a resiliently deformable band, said band being disposed circumferentially about said elongate tubular member.

6. The device of claim 5 wherein said wall of said elongate tubular member is axially reinforced.

7. The device of claim 5 wherein said wall of said elongate tubular member includes an axially extending coil.

8. The device of claim 5 wherein said elongate tubular element further provides a stenting function.

9. An endourethral device comprising:
   a. a first elongate tubular member positionable for communication with a bladder, said elongate tubular member having a wall, opposing first and second ends, and a lumen, said wall extending between said opposing first and second ends, said first end having at least one urine receiving orifice, said second end being an open end, said lumen joining said at least one urine receiving orifice with said second end;
   b. a second tubular element positionable within a bulbar portion of the urethra, said second tubular element adapted to receive and pass urine therethrough, said second tubular element being indirectly joined to said first tubular member;
   c. a first reversibly expandable element disposed circumferentially about, and longitudinally along said first tubular member, said first reversibly expandable element overlaying at least one fluid filling port in said wall of said elongated tubular member, said first reversibly expandable element being operatively engageable so as to expand and thereby anchor said elongate tubular member within a lower urinary tract;

d. a second reversibly expandable element disposed about, and longitudinally along said second elongate tubular member, said reversibly expandable element overlaying at least one fluid filling port in a wall of said second elongated tubular member; and, e. a fluid flow regulator interposed between said at least one fluid filling port and each of said reversibly expandable elements for regulating non-reversible fluid flow to said reversibly expandable element.

10. The device of claim 9 wherein said second reversibly expandable element is operatively engageable so as to expand and thereby anchor said second elongate tubular member within a lower urinary tract.

11. The device of claim 10 further comprising a sphincter responsive linkage extending from said first elongate tubular member to said second elongate tubular element.

12. The device of claim 11 wherein said sphincter responsive linkage comprises a conduit for receiving urine from said first elongate tubular member and discharging urine to said second elongate tubular member, said conduit being reversibly collapsible.

13. The device of claim 12 wherein said conduit is adapted to receive glandular fluids introduced into the urethra.

14. The device of claim 11 wherein said sphincter responsive linkage comprises a partially open channel for receiving and passing urine therethrough.

15. The device of claim 11 wherein said sphincter responsive linkage comprises a wire.

16. An assembly for treating urinary retention comprising:
a. an endourethral device deliverable into a lower urinary tract comprising an elongate tubular member and a reversibly expandable element disposed circumferentially about, and longitudinally along a portion of said tubular member, said tubular member adapted to permit fluid expansion of said reversibly expandable element, said reversibly expandable element being adapted to selectively reverse said fluid expansion; and,
b. an insertion tool for deploying said endourethral device in a lower urinary tract, said insertion tool comprising a elongate body having opposing first and second ends, a wall traversing said opposing first and second ends, sealing elements disposed circumferentially about a portion of said wall of said elongate body in the vicinity of said fluid transferring orifice such that urine received within said elongated tubular member is prohibited from passage through said wall of said elongate tubular member, and a device receiving portion longitudinally extending from said first end of said elongate body, said wall of said elongate body includes at least one fluid transferring orifice positioned within said device receiving portion of said elongate body, said device receiving portion being adapted to pass fluid from a fluid passageway longitudinally extending from said second end of said body to said reversibly expandable element of said device in furtherance of anchoring said elongate tubular member within the lower urinary tract, said insertion tool further comprising a sleeve adjacent said device receiving portion, said sleeve radially extending from a longitudinal axis of said insertion tool such that receipt of said endourethral device upon said device receiving portion of said tool in abutting engagement with said sleeve defines an assembly insertion form.

17. The assembly of claim 16 wherein said assembly insertion form is substantially uniform about said longitudinal axis of said insertion tool.

18. The assembly of claim 17 wherein said sleeve supports a device tether retainer.

19. The assembly of claim 18 wherein said insertion tool further comprises a longitudinally extending reinforcement element.

20. A prostatic urethral stent comprising a body for supporting at least a portion of a prostatic urethra, an anchor cuff supported by a portion of said body, and a retrieval mechanism extending from an end portion of said body, said body adapted so as to permit selective expansion of said anchor cuff in furtherance of forming an interference fit for said anchor cuff with a bladder neck subsequent to stent deployment, said retrieval mechanism including an anchor cuff plug for selective removal from a fluid egress port for said anchor cuff so as to permit contraction of an expanded anchor cuff in furtherance of deforming the interference fit for said anchor cuff wherein said anchor cuff is a first anchor cuff supported at a first portion of said body, a second anchor cuff being further supported by a second portion of said body.

21. The stent of claim 20 wherein said first and second body portions are adapted so as to permit selective expansion of said first and second anchor cuffs.

22. The stent of claim 21 in combination with an insertion tool for anchor cuff activation.

* * * * *

UNITED STATES PATENT AND TRADEMARK OFFICE
CERTIFICATE OF CORRECTION

| | | |
|---|---|---|
| PATENT NO. | : 7,141,038 B2 | Page 1 of 1 |
| APPLICATION NO. | : 10/343894 | |
| DATED | : November 28, 2006 | |
| INVENTOR(S) | : Mark J. Whalen et al. | |

It is certified that error appears in the above-identified patent and that said Letters Patent is hereby corrected as shown below:

On Title Page, Item (75), please change "Lloyd K. Wihlard" to --Lloyd K. Willard--.

Signed and Sealed this

Thirteenth Day of February, 2007

JON W. DUDAS
*Director of the United States Patent and Trademark Office*